United States Patent [19]

Sorochenko et al.

[11] Patent Number: 4,711,239
[45] Date of Patent: Dec. 8, 1987

[54] ELECTROSURGICAL INSTRUMENT

[76] Inventors: Oleg A. Sorochenko, ulitsa Chaikovskogo, 33b, kv. 105; Igor F. Kondratiev, pereulok Jurievsky, 9, both of Kharkov, U.S.S.R.

[21] Appl. No.: 915,248
[22] PCT Filed: Jan. 25, 1985
[86] PCT No.: PCT/SU85/00009
§ 371 Date: Aug. 26, 1986
§ 102(e) Date: Aug. 26, 1986
[87] PCT Pub. No.: WO86/04226
PCT Pub. Date: Jul. 31, 1986
[51] Int. Cl.[4] ............................................. A61B 17/39
[52] U.S. Cl. ........................ 128/303.14; 128/303.17; 219/234
[58] Field of Search ................... 128/303.13–303.19, 128/305; 219/234

[56] References Cited
U.S. PATENT DOCUMENTS
3,746,814 7/1973 Lackey et al. .............. 128/303.14 X
4,043,342 8/1977 Morrison, Jr. ................. 128/303.14
4,307,720 12/1981 Weber, Jr. ................. 128/303.18 X FOREIGN PATENT DOCUMENTS
2101893 1/1983 United Kingdom ........... 128/303.18

Primary Examiner—Lee S. Cohen
Attorney, Agent, or Firm—Burgess, Ryan & Wayne

[57] ABSTRACT

An electrosurgical instrument of the invention comprises a body (3) and, arranged coaxially, a passive electrode (2) and an active electrode (1), of which the outer electrode is associated with the body (3) and the central electrode is traversable with respect to the outer electrode (2). The instrument is provided with a power actuator and a device for cleaning the central electrode (1) of carbon deposit, the device being interposed between the electrodes (1, 2) and being made as an insert of an insulating material and provided with a through hole to suit the diametrical size of the central electrode (1) which extends through the hole. The electrode (1) is rigidly coupled to the power actuator for being traversable with respect to the hole.

3 Claims, 8 Drawing Figures

ELECTROSURGICAL INSTRUMENT

TECHNICAL FIELD

The present invention relates to medical engineering and more specifically it concerns electrosurgical instruments.

BACKGROUND ART

Known in the present state of the art is an electrosurgical instrument which is comprised of two electrodes, i.e., a small-area active electrode serving as the working electrode proper, and a larger-area passive electrode (cf. the paper entitled "Application of biactive bipolar electrodes in electrosurgery" by S. M. Shamraevsky et al. in the journal "Vestnik khirurgii imeni I. I. Grekova", No. 1, pp. 66–67 issued in 1971) (in Russian).

It is common practice that the passive electrode is bandaged to the lateral surface of the left thigh, or put under the patient's back, whereas the active electrode is used to carry out the surgical procedure involved. In this case the current field lines are dispersed in the tissues, thus concentrating in low-resistance areas and passing by those featuring poor electric conductance.

Use of the aforesaid instrument involves no clear-cut borderline between coagulated and sound tissue and may inflict damage to some organs and tissues located distantly of the place of application of the active electrode. In addition, orientation of the coagulation process as for direction and depth is impeded, and burns are likely to occur at the place of the passive electrode application.

One more prior-art electrosurgical instrument is known to comprise a body and coaxial electrodes of which the outer passive one is rigidly held in the body, while the central active electrode is traversable with respect to the outer electrode (cf. U.S. Pat. No. 4,043,342, Class A 61 B 17/32 published in 1977).

The instrument enables the current field lines to be concentrated at the active electrode situated in close proximity to the passive electrode, whereby the working zone is reduced drastically which makes practicable to carry out single-point coagulation or fine dissection of a tissue, e.g., in layer-by-layer excision of the gastric wall.

However, when surgery is performed by the aforesaid heretofore-known instrument the latter is liable to get out of order rather quickly due to carbon deposition on the active electrode, which thus interferes with further surgical procedure. Therefore the instrument is to be cleaned of carbon deposit repeatedly in the course of surgery, which is carried out manually and involves withdrawal of the instrument from the working zone, thus prolonging the operating time and complicates the surgeon's job.

DISCLOSURE OF THE INVENTION

The principal object of the invention is to provide an electrosurgical instrument which, when applied for carrying out limited single-point coagulation or fine dissection of a tissue would incorporate means for automatic removal of carbon deposit from the active electrode in the course of surgery.

Said object is accomplished due to the fact that an electrosurgical instrument, comprising a body and co-axially arranged a passive and an active electrode of which the outer one is associated with the body, while the central electrode is traversable with reference to the outer electrode, according to the invention, is provided with a mechanical actuator and a device for cleaning the central electrode of carbon deposit, fashioned as an insert made of an insulant and interposed between the electrodes, said device having a through hole to suit the diametrical size of the central electrode which passes through said hole and is rigidly coupled to the mechanical actuator for traversing relative to said hole.

The mechanical actuator may be so constructed as to impart reciprocating motion to the central electrode lengthwise the axis of said hole.

It is expedient that the central electrode be shaped as a needle located in the hollow space of the cylinder-shaped body at the end of which the outer electrode is provided, said outer electrode being shaped as a nut thread-joined with the body and accommodating an insert made as a spring-actuated ball having a centre hole and serving as a device for cleaning the central electrode of carbon deposit.

It is also practicable that the mechanical actuator be so made as to impart rotation to the central electrode about its longitudinal axis and that the central electrode be provided also with a means for its traversing along the axis of said hole.

It is desirable that the insert be shaped as a collet grip.

An electrosurgical instrument according to the present invention provides for limited single-point coagulation and fine dissection of tissues accompanied by automatic cleaning of the active electrode working surface in the course of surgery. The electrosurgical instrument made according to the invention is capable of:

- cutting of tissues with the rotary active electrode, whereby the latter is efficiently cleaned by the tissue being dissected immediately in the course of surgery;

- reciprocating motion of the active electrode with respect to the cleaning device strictly along the electrode longitudinal axis, which enables the instrument to be cleaned without retracting its working portion from the line of cut, this being impacticable with the known instrument due to incessant deviation of the active electrode end from true axial direction in the course of cleaning;

- efficient cleaning of the active electrode surface with the air of the cleaning device which, unlike the heretofore-known one, is not liable to lose its useful properties due to attrition, since its permanent forcing against the surface being cleaned is ensured.

BRIEF DESCRIPTION OF THE DRAWINGS

In what follows the invention will now be disclosed in a detailed description of some specific exemplary embodiments thereof with reference to the accompanying drawings. According to the invention, in the drawings.

BEST MODE OF CARRYING OUT THE INVENTION

Figure 1:
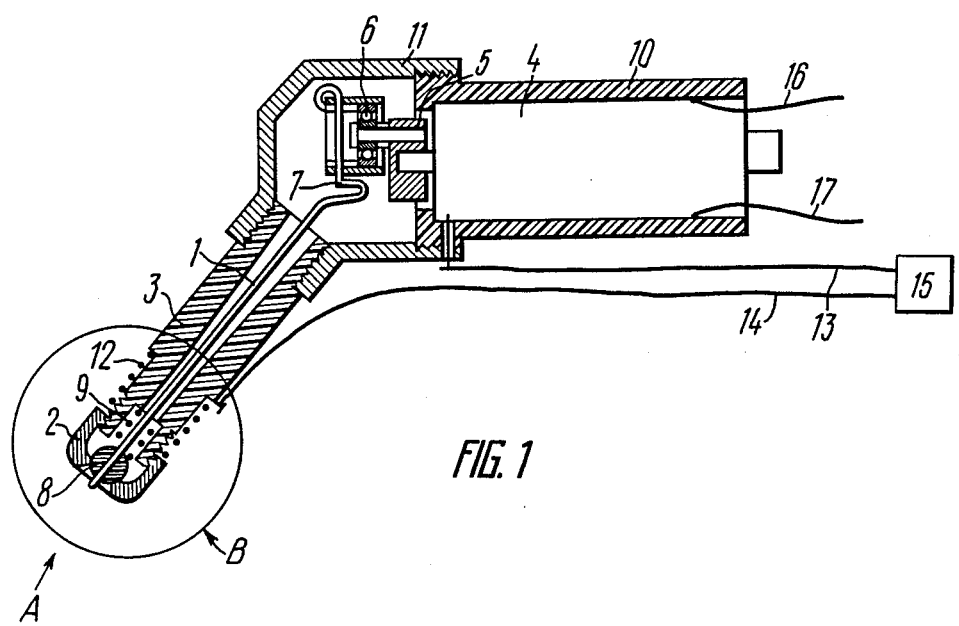
FIG. 1 is a general longitudinal sectional view of an electrosurgical instrument.

The electrosurgical instrument comprises an active central electrode 1 (FIGS. 1, 2, 3) shaped as a needle, and an outer passive electrode 2 arranged coaxially with the electrode 1 and made as a nut which is thread-joined with the end of a cylinder-shaped body 3. The interior space of the body 3 accommodates the electrode 1. In addition, the instrument incorporates a power drive comprising an electric motor 4 whose shaft mounts a crank 5 and a bearing 6 secured on the latter. The outer race of the bearing 6 carries the end of the active electrode 1 which is rigidly held to it and has a springy loop 7. The other (working) end of the active electrode 1 passes through the hole in an insert, which is essentially a ball 8 in the embodiment under consideration, made of an insulating material and inperposed between the electrodes 1 and 2 inside the nut and forced to it with a spring 9. The ball 8 functions as a device for cleaning the electrode 1 of carbon deposit. The hole in the ball 8 is equal in size with the diameter of the needle-shaped electrode 1. A housing 10 of the electric motor 4 is associated with the cylinder-shaped body 3 through an adapter 11. A metallic spring 12 is provided for locking the nut (of the electrode 2). Diathermic current is supplied to the electrodes 1 and 2 through current leads 13 and 14, respectively from a diathermic current source 15. Current leads 16 and 17 are provided for connection of the electric motor 4 to a power source (omitted in the Drawings).

Figure 4:
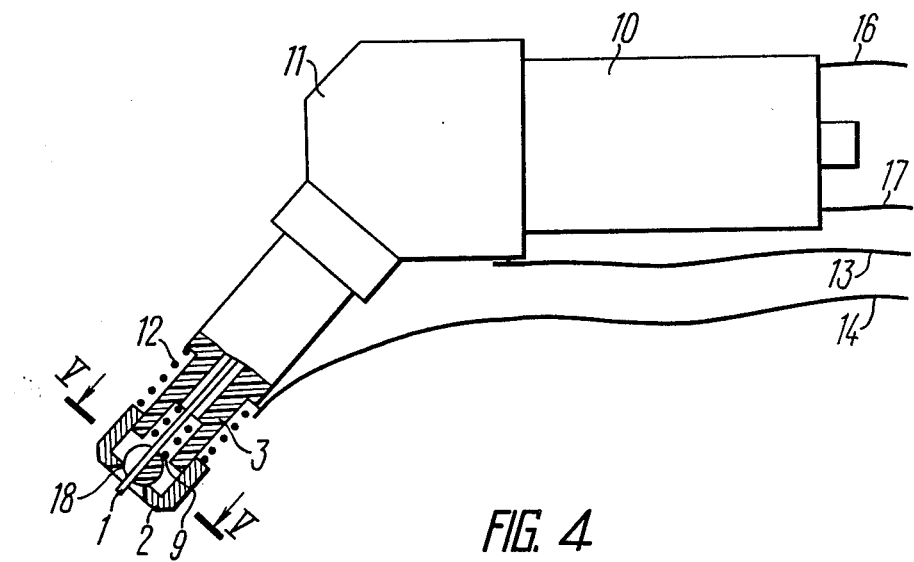
FIG. 4 is fragmentarily cutaway a view of FIG. 1 showing an embodiment with the insert made as a collet grip.
Figure 5:
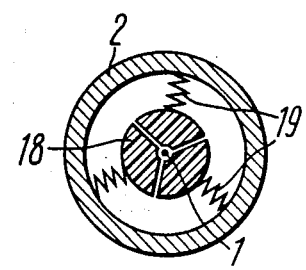
FIG. 5 is a scaled-up section taken along a line V—V in FIG. 4.

FIGS. 4 and 5 illustrate an embodiment of the electrosurgical instrument featuring the insert made as a three-jaw collet grip 18 whose jaws are loaded with springs 19. The collet grip 18 is made of a dielectric material.

Figure 6:
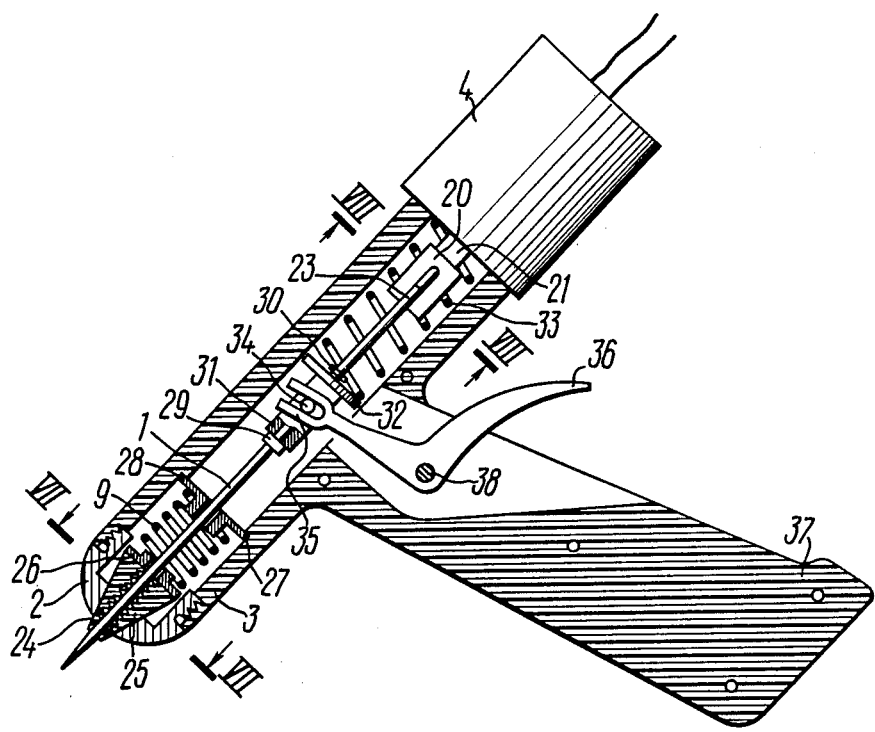
FIG. 6 is a sectional view of an embodiment of the electrosurgical instrument provided with a rotary motion mechanical actuator.
Figure 7:
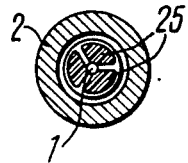
FIG. 7 is a section taken along a line VII—VII in FIG. 6.
Figure 8:
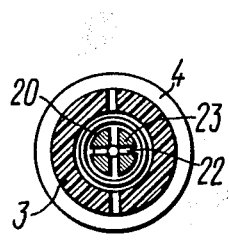
FIG. 8 is a section taken along a line VIII—VIII in FIG. 6.

In an alternative embodiment of the electrosurgical instrument represented in FIGS. 6, 7, 8 unlike the embodiments shown in FIGS. 1 to 5, the active central electrode 1 is associated, through a coupling 20, to an output shaft 21 of the electric motor 4 from which rotation is imparted to the electrode 1. To this end, longitudinal slots in the coupling 20 accommodate the arms 22 of a spider 23 secured at the nonworking end of the active electrode 1. The insert functioning as the device for cleaning the electrode 1 is fashioned in this embodiment of the instrument as a collet grip 24. Thus, the working end of the active electrode is clamped in the collet grip 24 which consists of three jaws 25 made of a dielectric material, a step bearing 26 resting upon the jaws 25, a step bearing 27 resting upon an annular shoulder 28 provided in the interior of the cylindrical body 3, and the spring 9 interposed between the step bearings 26 and 27. Collars 29 and 30 are provided in the central portion of the active electrode 1, between which a slidable bushing 31 is set, said bushing being provided with an annular ridge 32 at its end facing the electric motor 4. A return spring 33 is fitted between the annular ridge 32 of the slidable bushing 31 and the housing of the electric motor 4, said spring forcing the bushing 31 against the collar 29. The slidable bushing 31 is provided with two journals 34 accommodated in a fork 35 of a lever 36 articulately connected to a handgrip 37 of the instrument through a pivot 38. The handgrip 37 is rigidly attached to the cylinder-shaped body 3.

It is the electric motor 4 with the output shaft 21, the coupling 20 and the spider 23 that provide for continuous rotation of the active electrode 1. The lever 36, the slidable bushing 31 with the annular ridge 32 and the journals 34, the collars 29, 30 and the return spring 33 taken together establish the means for traversing the active electrode 1 along the axis of symmetry (hole) of the collet grip 24.

The electrosurgical instrument of the invention operates as follows.

Prior to surgery the electrodes 1 and 2 are set in relative position to each other so as to suit the required depth of penetration of the active electrode 1 (FIGS. 1, 2, 3) in the tissue being operated upon, which is attained by screwing the nut onto the body 3 until the required mutual arrangement of the electrodes is attained. This done, the nut is locked in place with the spring 12.

The working end of the active electrode (FIGS. 1, 2, 3) and the circular portion of the passive electrode 2 are so positioned at the place of surgery that the active electrode 1 is situated at a preset point or on the line of cut and that the passive electrode 2 is in a reliable contact with the living tissue surrounding the active electrode 1, whereupon diathermic current is supplied to said electrodes 1 and 2 from the source 15 through the current leads 13, 14.

Figures 2, 3:
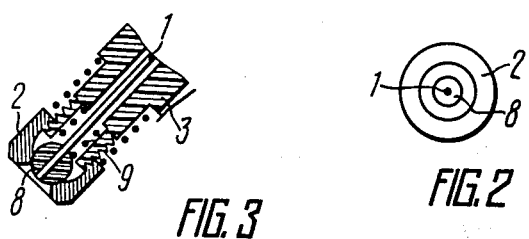
FIG. 2 is a view, facing arrow A, of the working portion of the electrosurgical instrument of FIG. 1.
FIG. 3 is a view of an area B in FIG. 1 showing the central electrode in a retracted position.

When a single-point microsurgery is performed, e.g. on a cerebral tumor, the active electrode 1 destroys the living tissue and penetrates thereinto for a depth depending on the amount of overhang of its working end relative to the passive electrode 2. Concurrently with the penetration of the active electrode 1 into the living tissue, there occurs electrocoagulation of the blood and lymphatic vessels, whereby the surgical procedure is a bloodless one. Once the tumor has been destroyed the instrument is withdrawn from the operative zone. Should carbon deposit be found to have formed on the active electrode 1, the electric motor 4 is switched on with the result that the electrode 1 receives reciprocating and oscillating motions, thus being cleaned of carbon deposit while interacting mechanically with the edge and faces of the hole in the ball 8. FIGS. 1 and 3 illustrate the electrode 1 while in its extreme positions, respectively.

When performing fine dissection of a tissue, e.g., in layer-by-layer excision of the gastric wall, penetration of the active electrode 1 into the living tissue is followed by moving the instrument along the line of cut, thus dissecting, e.g., the gastric mucosa bloodlessly. To remove carbon deposit from the surface of the active electrode 1 as fast as it is formed, the electric motor 4 is switched on periodically to clean the electrode surface of carbon deposit. As a rule, the cutting process involved in microsurgical procedures is not combined with the cleaning of the active electrode, i.e., the instrument, while being cleaned, is not traversed along a preset line of dissection. However, the instrument need not be withdrawn from the dissection zone for cleaning.

The embodiment of the electrosurgical instrument illustrated in FIGS. 4 and 5 operates in the same way as described hereinbefore with the sole exception that the collet grip 18 provides for better cleaning of the electrode 1 of carbon deposit within a shorter lapse of time.

The electrosurgical instrument represented in FIGS. 6, 7, 8 operates as follows.

Prior to surgery the depth of penetration of the electrode 1 into the living tissue is preset, in a way similar to that described above, that is, by changing its position relative to the passive electrode 2 by moving the latter on the thread of the body 3. Then the electric motor 4 is energized with the result that rotation of the output shaft 21 of the electric motor 4 is translated, via the coupling 20 and the spider 23, to the needle of the active electrode 1.

While rotating the active electrode 1 destroys the living tissue and penetrates thereinto for a depth which depends on the amount of overhang of its working end with respect to the passive electrode 2. Concurrently with the penetration of the electrode 1 into the living tissue, there occurs electrocoagulation of the blood and lymphatic vessels, whereby the surgical procedure is carried out bloodlessly.

During surgery the continuously rotating needle of the active electrode 1 self-cleans due to a permanent sliding contact with the compacted living tissue. However, an additional mechanical cleaning of the active electrode 1 is to be resorted to in the case of a prolonged surgical procedure, or when dissecting badly bleeding tissues, use being made of a device imparting reciprocating motion to the active electrode 1 with respect to the axis of symmetry of the collet grip 24. To this aim one should periodically depress the lever 36, which, while turning about the pivot 38, urges the journals 34 of the slidable bushing 31 to move by virtue of the fork 35. The annular ridge 32 of the bushing 31 presses upon the collar 30 provided on the active electrode 1, thus compressing the return spring 33 and causing the needle of the active electrode 1 to move towards the electric motor 4. As a result, the arms 22 of the spider 23 slide along the longitudinal slots of the coupling 20, and the working end of the active electrode 1 is pulled, while rotating, through the jaws 25 of the collet grip 24, thus getting rid of carbon deposit efficiently. The return stroke of the active electrode 1 (i.e., away from the electric motor 4) is actuated by the return spring 33 which forces the slidable bushing 31 against the collar 29 as soon as the lever 36 is released. Thus, the lever 36 should be given several depressions to completely clean the instrument of carbon deposit.

It is due to the active electrode 1 traversing strictly along its longitudinal axis that mechanical cleaning of the instrument can be carried out without withdrawing the instrument from the operative zone. Continuous rotation of the active electrode 1 promotes its efficient self-cleaning by the compacted tissue and simplifies much its power-assisted cleaning with the aid of the collet grip 24. Use of the collet grip 24 provides for continuous reliable contact of the jaws 25 with the surface being cleaned of the active electrode even when the jaws 25 are somewhat worn.

Reciprocating motion of the active electrode 1 can be still more eased compared with the aforedescribed construction, when the active electrode 1 is rigidly coupled to the output shaft 21 of the electric motor 4, and the housing of the electric motor 4 is traversed by means of the lever and the return spring 33 (such an embodiment being omitted in the Drawings).

INDUSTRIAL APPLICABILITY

The electrosurgical instrument of the invention can find widespread application in microsurgery, as well as for performing bloodless plastic surgery on the gastrointestinal tract, urinary system, the lungs, and some other organs.

We claim:

1. An electrosurgical instrument, comprising:
   a cylinder-shaped body having an interior;
   a passive outer electrode mounted to an end of the cylinder-shaped body in coaxial relation therewith and made as a nut thread-joined with the body;
   an active central electrode shaped as a needle located in the interior of the cylinder-shaped body coaxially with the outer electrode and traversable with respect to the outer electrode;
   means for cleaning carbon deposits from said central electrode, said means including an insert made of an insulating material and accommodated inside the outer electrode, the insert being made as a spring-actuated ball having a central hole through which the central electrode is passed, the ball hole having an axis and a diameter equal to the diameter of the central electrode; and
   a power actuator rigidly coupled to the central electrode to impart reciprocating motion to the central elctrode along the axis of the ball hole.

2. An electrosurgical instrument, comprising;
   a cylinder-shaped body having an interior;
   a passive outer electrode mounted to an end of the cylinder-shaped body in coaxial relation therewith;
   an active central electrode located in the interior of and coaxial with the cylinder-shaped body and traversable with respect to the outer electrode;
   means for cleaning carbon deposits from said central electrode, said means including an insert made of an insulating material and accommodated inside the outer electrode, the insert having a central hole through which the central electrode is passed, the insert hole having an axis and a diameter equal to the diameter of the central electrode;
   a power actuator rigidly coupled to the central electrode to impart rotational movement to the central electrode about its longitudinal axis; and
   additional means for causing said central electrode to traverse along the axis of said hole.

3. An electrosurgical instrument, comprising;
   a cylinder-shaped body having an interior;
   a passive outer electrode mounted to an end of the cylinder-shaped body in coaxial relation therewith;
   an active central electrode located in the interior of and coaxial with the cylinder-shaped body and traversable with respect to the outer electrode;
   means for cleaning carbon deposits from said central electrode, said means including an insert made of an insulating material and accommodated inside the outer electrode, the insert being made as a collet grip through which the central electrode is passed;
   a power actuator rigidly coupled to the central electrode to impart rotational movement to the central electrode about its longitudinal axis; and
   additional means for causing said central electrode to traverse along the axis of said hole.

* * * * *